(12) United States Patent
Bachman et al.

(10) Patent No.: US 6,860,890 B2
(45) Date of Patent: Mar. 1, 2005

(54) SURGICAL KNOT PUSHING DEVICE AND METHOD OF USE

(75) Inventors: Alan B. Bachman, New Haven, CT (US); William J. Allen, Stratford, CT (US); Frederick T. Karl, Bethel, CT (US); Robert R. Steckel, Norwalk, CT (US)

(73) Assignee: Edwards Lifesciences Corporation, Irvine, CA (US)

( * ) Notice: Subject to any disclaimer, the term of this patent is extended or adjusted under 35 U.S.C. 154(b) by 212 days.

(21) Appl. No.: 09/797,964

(22) Filed: Mar. 2, 2001

(65) Prior Publication Data

US 2002/0123758 A1 Sep. 5, 2002

(51) Int. Cl.[7] .............................................. A61B 17/04
(52) U.S. Cl. ...................................................... 606/148
(58) Field of Search ........................................ 606/148

(56) References Cited

U.S. PATENT DOCUMENTS

| | | | |
|---|---|---|---|
| 4,636,202 A | | 1/1987 | Lowin et al. |
| 5,084,058 A | | 1/1992 | Li |
| 5,133,723 A | * | 7/1992 | Li et al. ........................ 289/17 |
| 5,163,946 A | | 11/1992 | Li |
| 5,176,691 A | | 1/1993 | Pierce |
| 5,242,459 A | | 9/1993 | Buelna |
| 5,423,837 A | | 6/1995 | Mericle et al. |
| 5,439,470 A | | 8/1995 | Li |
| 5,549,618 A | * | 8/1996 | Fleenor et al. ............... 606/148 |
| 5,752,964 A | | 5/1998 | Mericle |
| 5,755,730 A | | 5/1998 | Swain et al. |
| 5,827,300 A | | 10/1998 | Fleega |
| 5,906,577 A | | 5/1999 | Beane et al. |
| 5,984,939 A | | 11/1999 | Yoon |
| 6,132,439 A | | 10/2000 | Kontos |
| 6,152,934 A | | 11/2000 | Harper et al. |
| 6,260,552 B1 | | 7/2001 | Mortier et al. |

FOREIGN PATENT DOCUMENTS

| | | |
|---|---|---|
| DE | 41 36 861 A1 | 5/1993 |
| DE | 197 28 139 A1 | 1/1999 |
| EP | 0706779 A1 | 4/1996 |
| WO | WO94/08515 | 4/1994 |
| WO | WO95/19139 | 7/1995 |
| WO | WO95/29636 | 11/1995 |
| WO | WO97/11642 | 4/1997 |
| WO | WO98/11825 | 3/1998 |
| WO | WO00/69342 | 11/2000 |

* cited by examiner

*Primary Examiner*—John J. Calvert
*Assistant Examiner*—James G Smith
(74) *Attorney, Agent, or Firm*—David L Hauser

(57) ABSTRACT

A surgical knot pushing device is described which has a knot pushing interface mounted on the distal portion of an elongated body and an actuation handle located on the proximal portion of the elongated body. The knot pushing interface has a suture receiving recess formed thereon, and a knot positioning member which traverses the suture receiving interface. At least one extendable knot retaining member is further positioned on the pushing interface, the at least one extendable retaining member capable of engaging suture material. The knot pushing interface also comprises at least one suture cutting member which is in communication with the actuation handle. The present invention is particularly well suited for use in minimally invasive surgical procedures. The present invention also teaches a method of forming a knot in suture material, retaining a knot with a knot pushing device, advancing and applying a knot to an area of interest, and cutting excess suture material.

18 Claims, 11 Drawing Sheets

SURGICAL KNOT PUSHING DEVICE AND METHOD OF USE

BACKGROUND OF THE INVENTION

Minimally invasive surgical techniques have emerged as an alternative to conventional surgical techniques to perform a plurality of surgical procedures. Minimally invasive procedures differ from conventional surgical procedures in that a plurality of devices may be introduced into the body through a small incision. As a result, trauma to the body is greatly reduced, thereby decreasing the recovery time of the patient.

Many conventional surgical procedures have been performed using minimally invasive techniques. One challenge presented when performing a heretofore conventional surgical procedure using a minimally invasive technique is to remotely position and apply sutures to an area of interest. Commonly, a suture will be required to approximate at least two pieces of tissue. In conventional surgical techniques, the surgeon will approximate the tissue pieces by forcing a needle and suture material through various portions of the tissue to be approximated, and tying a knot in the suture material resulting in approximation. In contrast, in minimally invasive surgical techniques the surgeon's access to the approximation site is greatly reduced. Commonly, a surgical device will attach the suture material to the tissue. The surgeon will remotely form a knot in the suture material and advance the knot to the area of interest with a "knot pusher," thereby approximating the tissue. Thereafter, the knot pusher is removed from the body and a suture cutting device is inserted to cut the surplus suture material.

Several knot pushing devices are known. These devices permit an operator to push suture knots which have been formed extracorporeally towards tissue to be sutured. For example, U.S. Pat. No. 5,769,863, issued to Garrison et al., discloses a surgical knot pusher having an elongated body connected to a pushing head. The pushing head engages a portion of suture material containing a knot and is advanced to the area of interest, thereby "throwing" the knot. Once the suture knot is placed the knot pushing device is removed and a cutting implement is introduced into the body and cuts the remaining suture material. The remaining suture material is then removed. The device disclosed therein failed to effectively address the cutting of superfluous suture material, instead requiring the use of a supplemental cutting implement to be precisely positioned proximate the suture knot.

With respect to the aforementioned devices, it is desirable to have a system capable of intracorporeally positioning and applying a suture knot to an area of interest. Additionally, it is desirable to have a knot pushing system wherein the operator may cut and remove surplus suture material using the knot pushing device.

BRIEF SUMMARY OF THE INVENTION

The present invention solves the problem of effectively delivering a knot formed outside the body from surgical suture material to a location proximate to a repair site in vivo. Additionally, the present invention provides a device capable of delivering the suture knot to a intracorporeal location and cutting excess suture material, thereby effectively approximating tissue pieces.

The knot pushing device of the present invention is optimized for use in minimally invasive surgical procedures wherein the surgeon's access to the area of interest is greatly reduced. Additionally, the knot pushing device of the present invention may be used to advance a plurality of bi-manually formed surgical knots utilized in conventional surgical procedures. The knot pushing device disclosed herein may be further used to sequentially advance multiple knots or "throws" to the repair area.

In one aspect, the present invention provides a knot pushing device comprising an elongated body having a distal portion attached to a pushing interface and a proximal portion attached to an actuation handle. The elongated body may be manufactured from a plurality of materials depending on the desired use.

The pushing interface comprises at least one suture cutting member which is in communication with the actuation handle. The at least one suture cutting member enables an operator to deliver a suture to a site of repair, apply the suture, and remove excess suture material with one device.

Also disclosed herein is a knot pushing device capable of mechanically retaining the suture knot and suture material, advancing the knot down the suture material, applying the knot to an area of interest, and removing excess suture material. The present embodiment comprises an elongated body having a distal portion attached to a pushing interface and a proximal portion attached to an actuation handle. The pushing interface comprises at least one cutting member and at least one extendable retaining member capable of capturing, retaining, and releasing suture material.

The present invention further discloses a method of forming a knot from surgical suture material, advancing the knot to a location in vivo, applying the suture to an area of repair, and removing excess suture material.

Other objects and further features of the present invention will become apparent from the following description when read in conjunction with the attached drawings.

DESCRIPTION OF THE PREFERRED EMBODIMENTS

Disclosed herein is a description of various illustrated embodiments of the invention. This description is not to be taken in a limiting sense, but is made merely for the purpose of illustrating the general principles of the invention. The section titles and overall organization of the present description are for the purpose of convenience only and are not intended to limit the present invention.

The knot pushing device of the present invention is generally used in minimally invasive surgical procedures, which typically utilize relatively small incisions, to precisely apply and position a knot. The device and method disclosed herein are of particular value when a surgeon or other clinician is unable to tie a suture knot directly at the surgical site. The device has particular relevance to the surgical procedures disclosed in co-pending U.S. patent application Ser. No. 09/562,406 filed on May 1, 2000 entitled Minimally Invasive Mitral Valve Repair System and Method and U.S. patent application entitled Method And System For Tissue Repair Using Dual Catheters filed on Feb. 6, 2001, both of which have been assigned to the assignee of the present invention and which are incorporated by reference as if set forth herein in their entirety. Those skilled in the art will appreciate, however, that the device and method are relevant to a variety of procedures wherein a surgeon's hands cannot directly reach the surgical site.

As those skilled in the art will appreciate, the present invention may be utilized as a handheld device or, in the alternative, as a catheter delivered implement. It is anticipated as being within the scope of the present invention to produce a knot pusher capable of functionally delivering knots formed with a plurality of suture sizes to various locations within a body.

Figure 1:
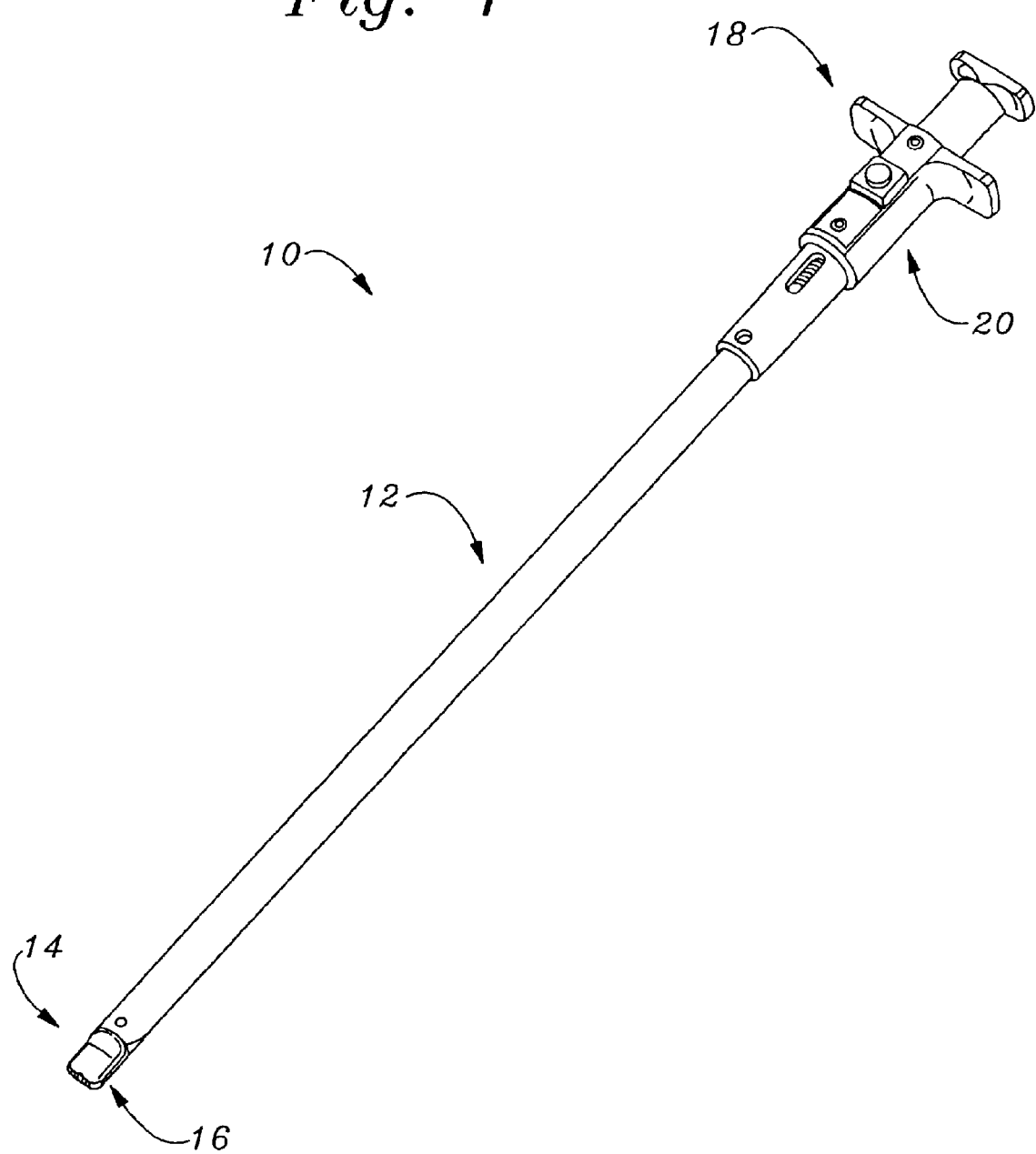
FIG. 1 is an elevated view of the surgical knot pushing device of the present invention.

Referring to FIG. 1 of the drawings, the device 10 comprises an elongated body member 12 having a distal portion 14 attached to a pushing interface 16 and a proximal portion 18 having an actuation handle 20 attached thereto. The elongated body member 12 of the present invention may be manufactured in a plurality of lengths, as required.

Those skilled in the art will appreciate that the elongated body member 12 may be manufactured from a plurality of materials, including, for example, polycarbonate or polyacetate, thereby providing a relatively rigid device. In an alternative embodiment of the present invention, the elongated body member 12 may be manufactured from moderately flexible materials such as, for example, polyvinyl chloride or braided cable, thereby enabling catheter-based applications. Alternatively, the elongated body 12 of the present invention may contain at least one internal lumen.

Figure 2:
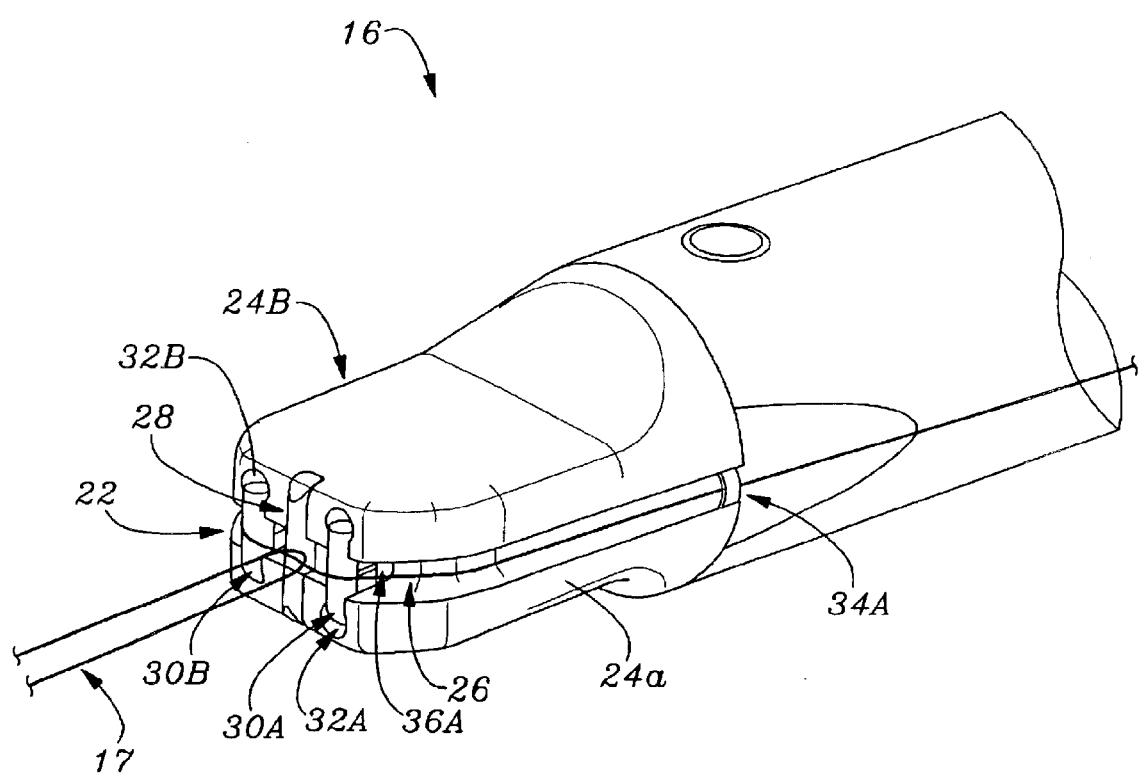
FIG. 2 is an elevated view of the pushing interface of the surgical knot pushing device engaging suture material.

FIG. 2 shows the pushing interface 16 of the present invention engaging a portion of suture material 17. As shown in FIG. 2, the pushing interface 16 comprises a distal face 22 and first and second sidewalls 24a and 24b. A suture receiving recess 26 containing suture material 17 extends from the first sidewall 24a, across the distal face 22, and traverses the second sidewall 24b. A knot positioning member 28, which is located on the distal face 22, is in communication with the suture receiving recess 26. In the illustrated embodiment, the knot pushing member 28 is a transverse member which engages and stabilizes a knot positioned thereon. During use, pulling tension is applied to the suture material 17 by the operator ensuring that the knot remains positioned on the knot positioning member 28, thereby permitting accurate knot placement. The distal face 22 further comprises at least one extendable retaining member. As illustrated in FIG. 2, two extendable retaining members 30a and 30b, shown in a retracted position, are positioned within retaining member receivers 32a and 32b, respectively. The elongated body 12 or pushing interface 16 may also be constructed with suture ports 34a and 34b, if desired. The suture ports 34a and 34b, if included, provide a barrier preventing the suture material 17 from becoming dislodged or displaced from the suture receiving recess 26.

The pushing interface 16 shown in FIG. 2 may be manufactured from a plurality of materials including, for example, stainless steel, titanium, ceramic, reinforced plastic, or other rigid biologically compatible materials capable of withstanding sterilization. In an alternate embodiment of the device 10, different materials may be used to manufacture various component of the pushing interface 16. For example, the pushing interface 16 may be manufactured from a reinforced plastic and the extendable retaining members 30a and 30b may be manufactured from stainless steel. Alternatively, the pushing interface 16 may include coatings, such as Teflon®, to reduce friction.

Figure 3:
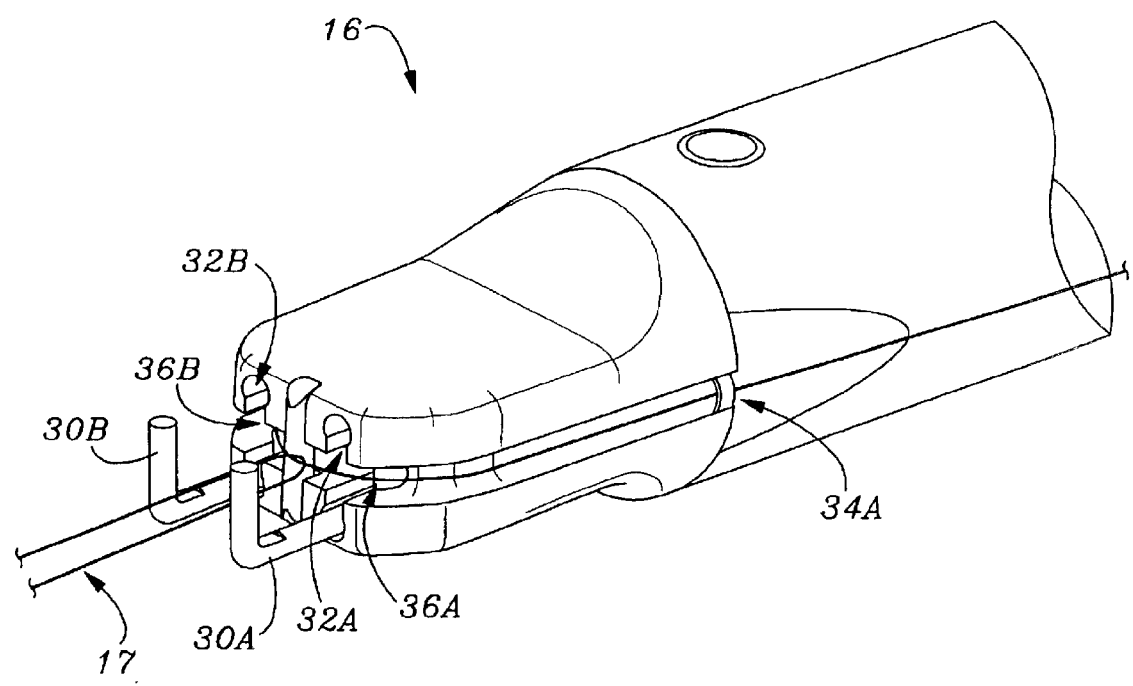
FIG. 3 is an elevated view of the pushing interface of the surgical knot pushing device having two extendable retaining members extended with suture material disposed thereon.

FIG. 3 shows the pushing interface 16 of the present invention having the extendable retaining members 30a and 30b extended, thereby preparing to retain suture material 17. As shown in FIG. 3, a pair of cutting members 36a and 36b are located within the retaining member receivers 32a and 32b. The cutting members 36a and 36b may be manufactured from a plurality of materials, including, without limitation, titanium, stainless steel, ceramic, or reinforced plastic. As shown in FIG. 3, the extendable retaining members 30a and 30b cooperatively engage the cutting members 36a and 36b, thereby ensuring effective cutting of any material positioned therebetween.

Figure 4:
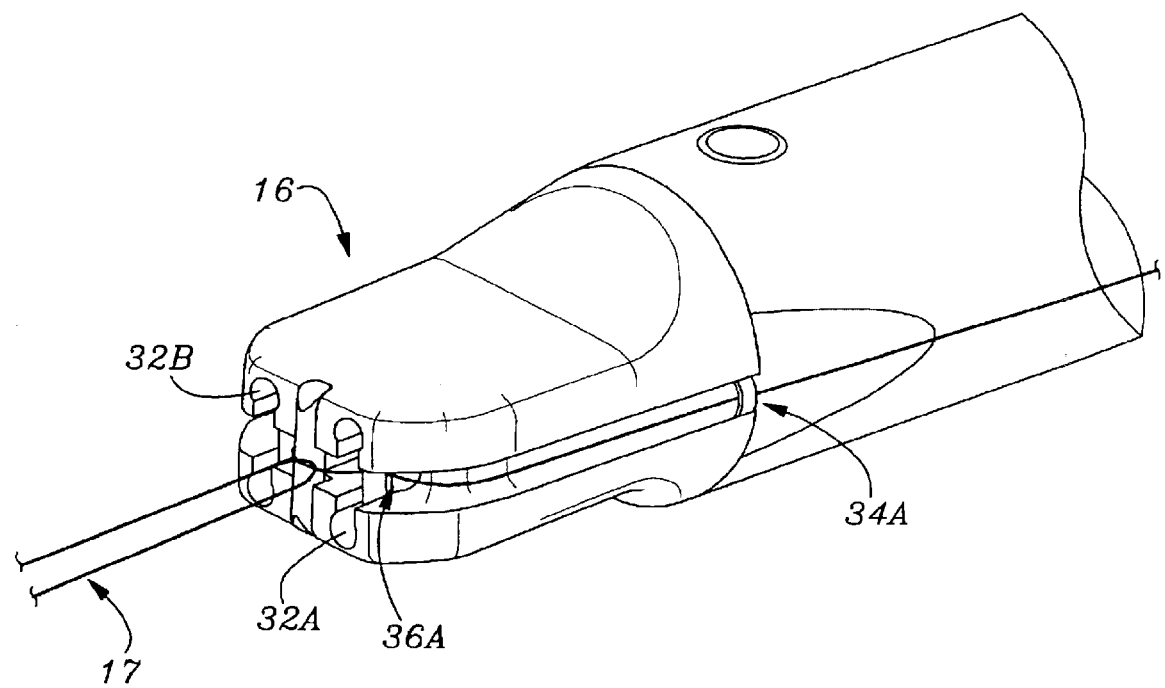
FIG. 4 is an elevated view of the pushing interface of the surgical knot pushing device retaining and cutting suture material.

As illustrated in FIGS. 2–4, the extendable retaining members 30a and 30b have three positions: a retracted position wherein the retaining members 30a and 30b are positioned within the receiving recesses 32a and 32b as shown in FIG. 2; an extended position wherein said retaining members 30a and 30b extend beyond the distal portion of the pushing head 16 as shown in FIG. 3; and a cutting position wherein said retaining members 30a and 30b are retracted further within the retaining member receivers 32a and 32b to engage the cutting members 36a and 36b as shown in FIG. 4. As shown in FIG. 4, the extendable retaining members 30a and 30b are retracted further within the retaining member recesses 32a and 32b, thereby forcing the suture material 17 to engage the cutting members 36a and 36b.

Figure 5:
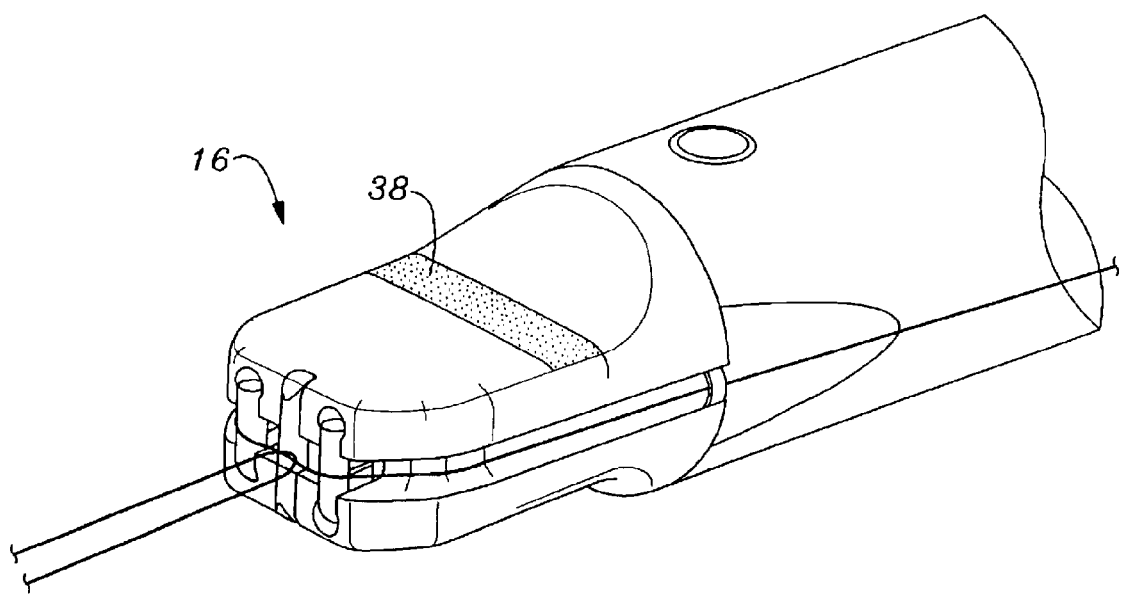
FIG. 5 is an elevated view of an alternate embodiment of the pushing interface of the surgical knot pushing device having a visualization device disposed thereon.
Figure 6:
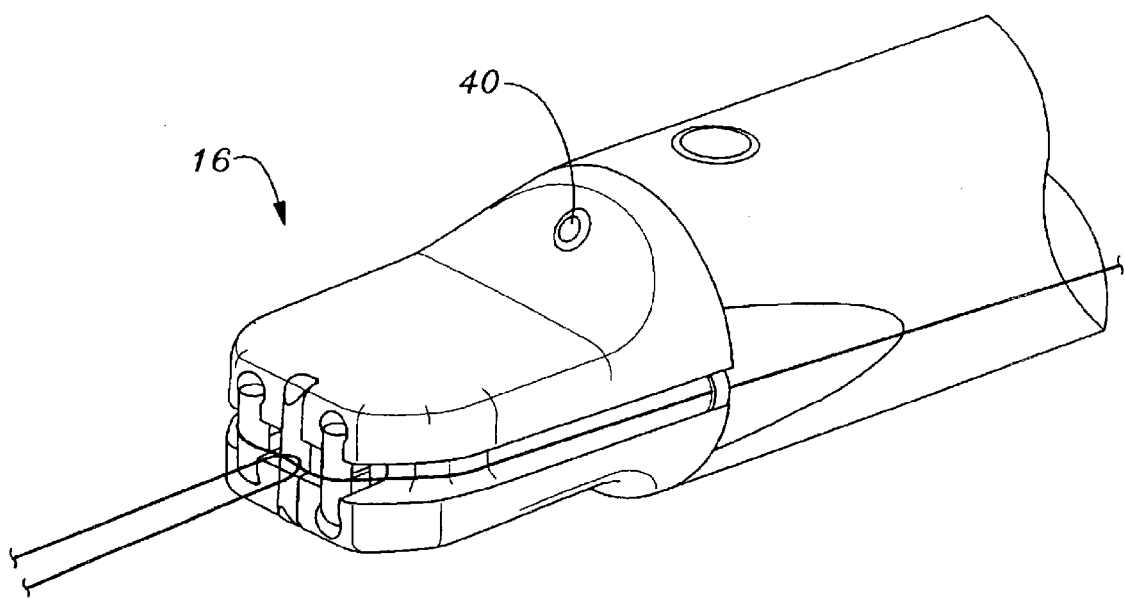
FIG. 6 is an elevated view of an alternate embodiment of the pushing interface of the surgical knot pushing device having a medicament application device disposed thereon.

Those skilled in the art of minimally invasive surgery will appreciate that the pushing interface 16 may comprise additional devices. As shown in FIG. 5, a visualization 38 device may be disposed on the pushing interface 16, thereby enabling the operator to visualize the suture placement. The visualization device 38 may be passive in the form of a radio-opaque or echo-genic material for visualization by x-ray or ultrasound. In an alternate embodiment, the visualization may be achieved with an ultrasonic or fiber optic probe coupled to the device. In an alternative embodiment as shown in FIG. 6, the pushing interface 16 may further comprise a medicament applicator 40 in communication with at least one medicament lumen (not shown) located within the elongated body 12, thereby enabling the delivery and application of a medicament to the tissue containing or surrounding the suture.

Figure 7:
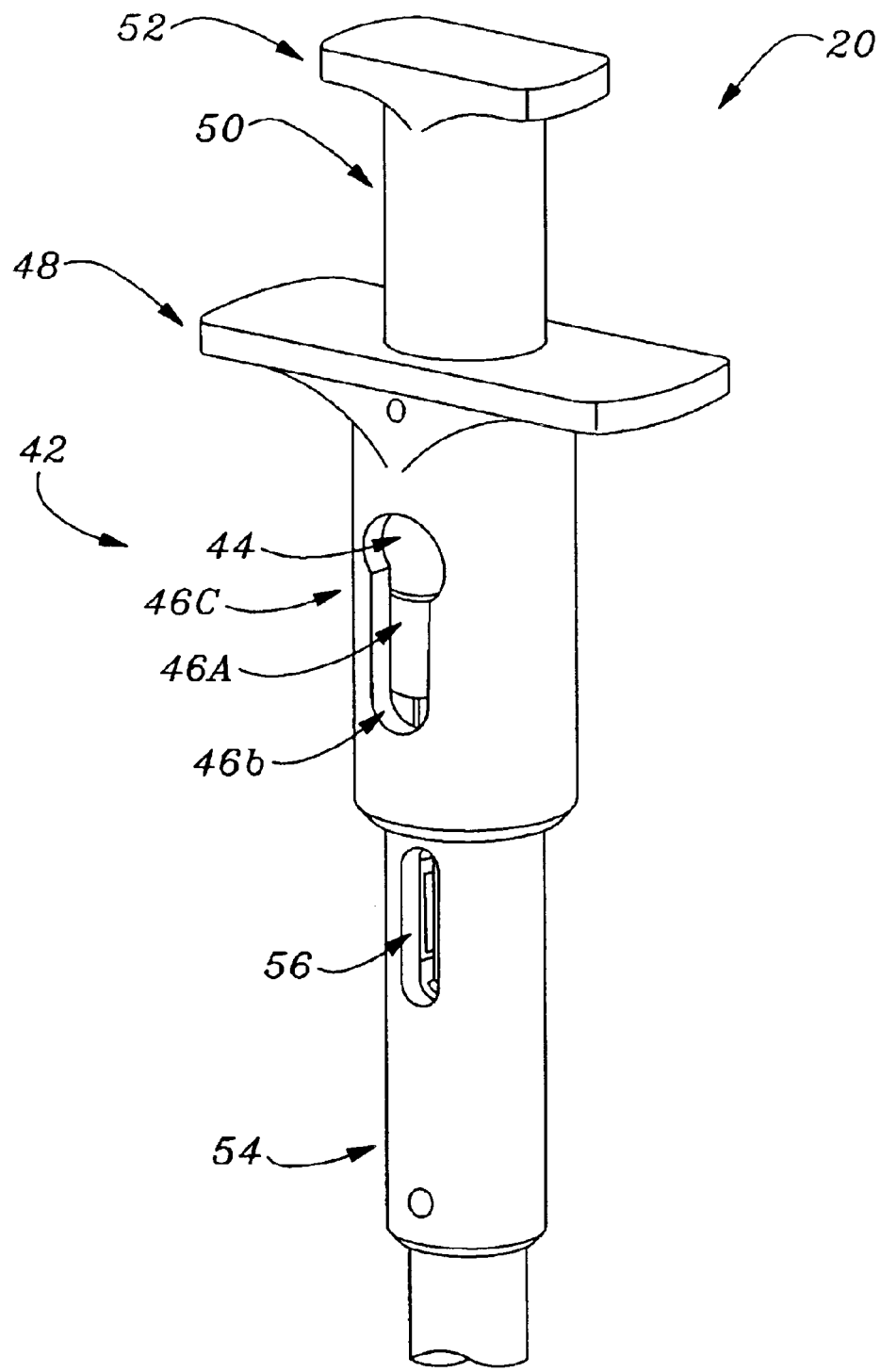
FIG. 7 is an elevated view of the actuation handle of the surgical knot pushing device.

FIG. 7 shows the exterior of the actuation handle 20 of the present invention. The actuation handle 20 comprises a handle body 42 having a cutting actuator 44 positioned within a cutting actuator receiver 46, an integral stop 48, a slidable actuation piston 50 having a pusher 52, and an actuation assembly 54 having an adjustment recess 56 formed therein. The actuation piston 50 is slidably coupled to the handle body 42 and is in communication with the extendable retaining members 30a and 30b. The cutting actuator receiver 46 forms a multiple lobe orifice having a first position 46a which corresponds to the extendable retaining members 30a and 30b being in a retained position; a second position 46b which corresponds to the extendable retaining members 30a and 30b being in an extended position; and a third position 46c which corresponds to the extendable retaining members 30a and 30b being in a cutting position. The adjustment recess 56 provides user access to the adjustment screws 66 and 70 (see FIG. 10), and the retaining members clamping assembly 64 (see FIGS. 9 and 10) positioned within the actuation handle. Those skilled in the art will appreciate that the actuation handle of the present invention may be manufactured from a plurality of materials, including, for example, reinforced plastic, various metals, and biologically compatible elastomers.

Figure 8:
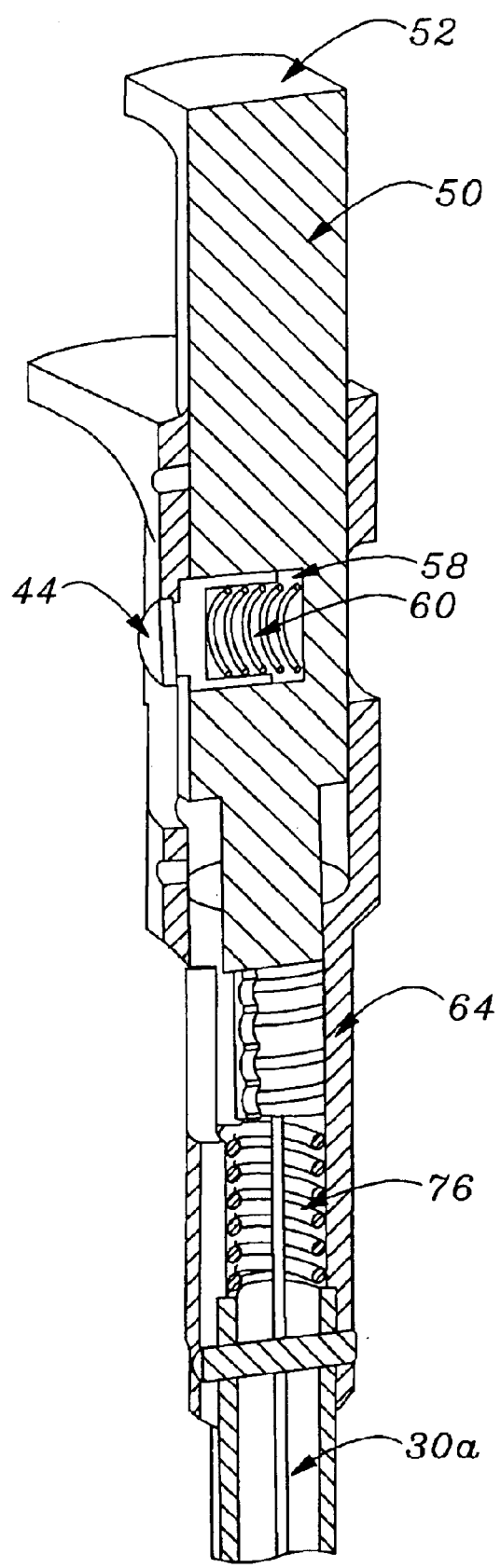
FIG. 8 is an sectional view of the actuation handle of the surgical knot pushing device showing the internal components.

FIG. 8 shows the internal components of the cutting actuation assembly positioned within the actuation handle 42. As shown in FIG. 8, the cutting actuator 44 is positioned within a cutting actuator channel 58 formed within the slidable actuation piston 50, and in communication with a cutting actuator biasing member 60 positioned therein.

Figure 9:
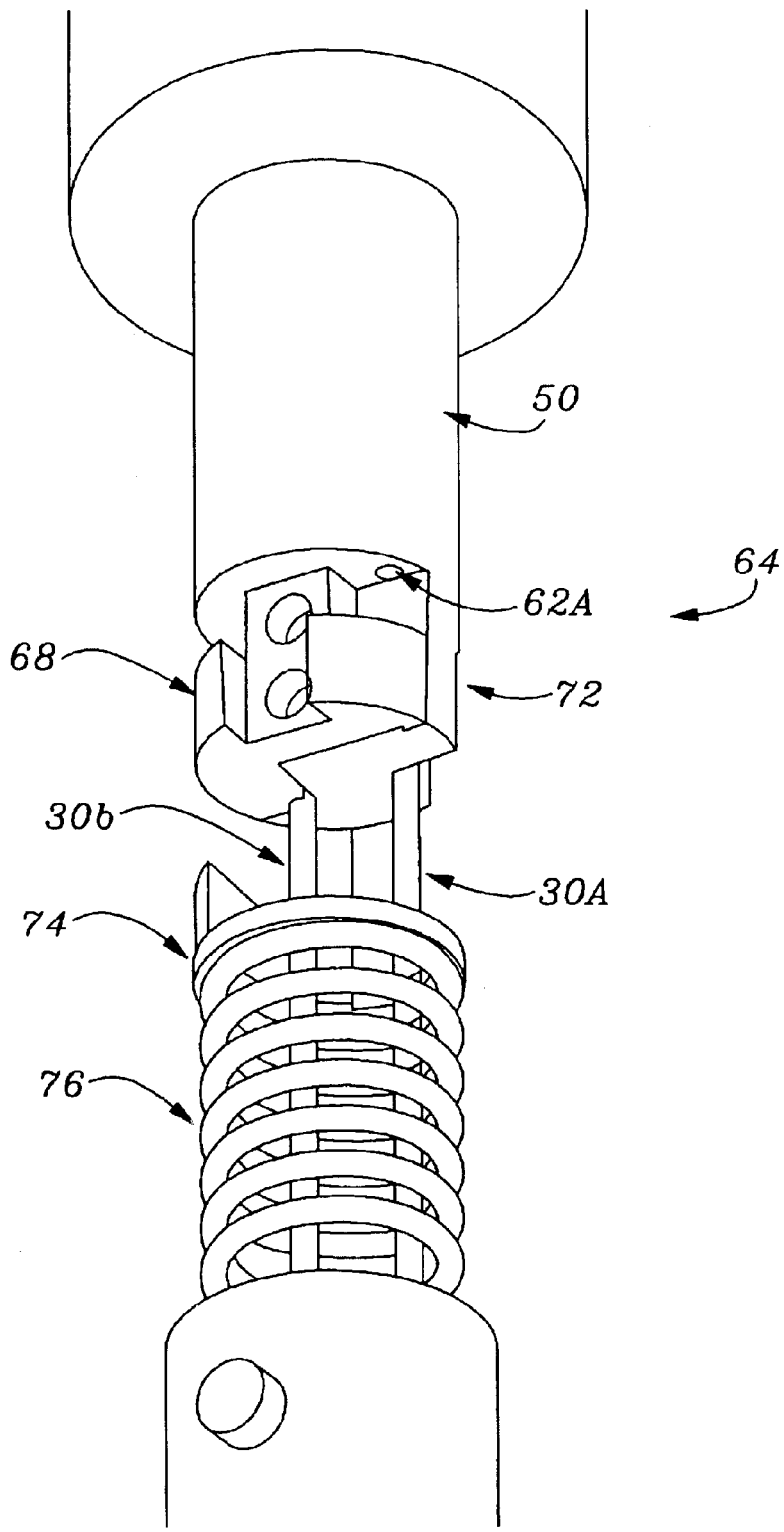
FIG. 9 is a perspective sectional view of the actuation handle of the surgical knot pushing device showing the internal components of the actuation system.
Figure 10:
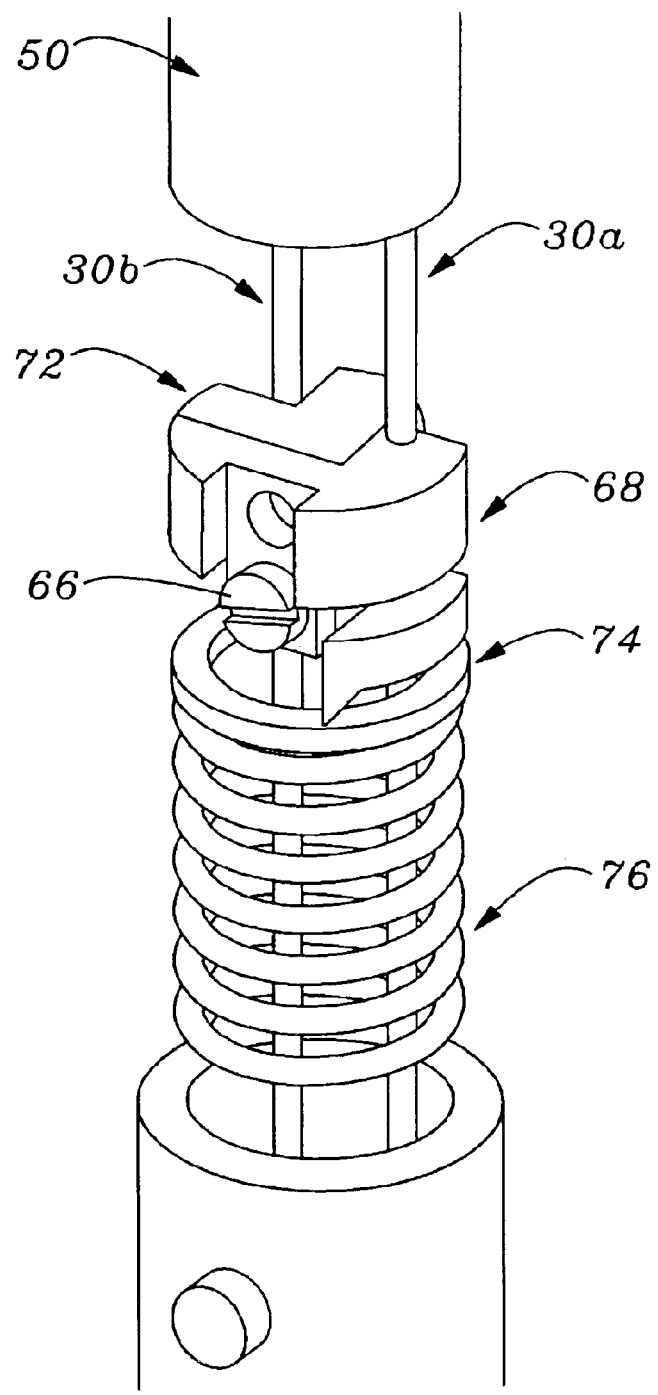
FIG. 10 is an elevated sectional view of the actuation handle of the surgical knot pushing device showing the internal components of the actuation system.

FIGS. 9–10 show two angular views of the internal actuation assembly of the present invention. As shown in FIG. 9, two retaining member ports 62a and 62b formed in the slidable actuation piston 58 receive the extendable retaining members 30a and 30b. The retaining members clamping assembly 64 comprises a first adjustment screw 66 coupled to a first clamp portion 68 and a second adjustment screw 70 coupled to a second clamp portion 72. The adjustment screws 66 and 70 permit the operator to adjust the extension and retraction action of the extendable retaining members 30a and 30b individually. For example, an operator may loosen the first adjustment screw 66 and manually retract the extendable retaining member 30b further into the actuation handle 20, thereby causing the extendable retaining member 30b to engage the cutting member 36b before the other extendable retaining member 30a engages the other cutting member 36a. Those skilled in the art will appreciate the capability to individually adjust the extendable retaining members 30a and 30b enables a consistent cutting action by the device. The retaining members clamping assembly 64 is positioned on the extendable retaining members 30a and 30b, proximate a washer 74 and a biasing member 76. The first clamp portion 68 and second clamp portion 72 cooperatively position and secure the retaining members 30a and 30b respectively. Retaining members 30a and 30b are secured between the first clamping portion 68 and the second clamping portion 70. The first and second clamping portions 68 and 72 are attached to each other with the adjustment screws 66 and 70 such that tightening the adjustment screws 66 and 70 decreases the distance between the first and second clamping portions 68 and 72, thereby securing the extendable retaining members 30a and 30b positioned therebetween. The bifurcated clamping assembly allows the operator to adjust the engagement of the extendable retaining member 30a and 30b relative to the cutting members (not shown), thereby ensuring effective cutting of the suture. The washer 74 and biasing member 76 forcibly bias the slidable actuation piston 50 to position the retaining members 30a and 30b is a retracted position.

Figure 11A:
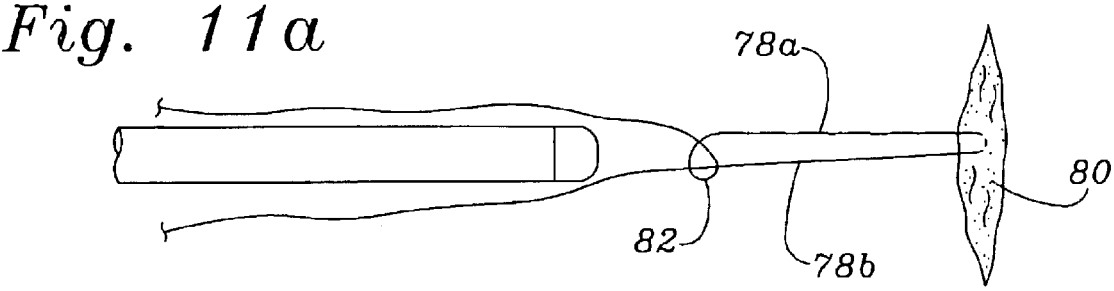
FIG. 11a is a side view of the knot pushing device of the present invention preparing to engage a knot being formed in suture material.
Figure 11B:
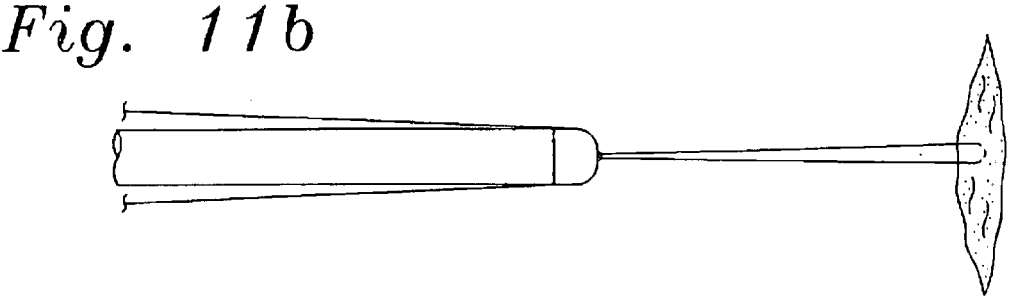
FIG. 11b is a side view of the knot pushing device of the present invention preparing to engage the knot formed in suture material.

The present invention further teaches various methods of using the knot pushing device disclosed herein. In a first embodiment, the device can be used to advance, or "throw" a knot to the approximated tissue. As shown in FIGS. 11a–11b, a portion of suture material 78, having opposite end portions 78a and 78b, is secured to various tissue pieces 80 to be approximated. A knot 82 is extracorporeally formed in the suture material 78 using a standard bimanual technique. The excess suture material 78a and 78b is then positioned within the suture receiving recess 26 along the pushing interface sidewalls 24a and 24b such that the knot 82 is positioned proximate the knot positioning member 28, and a pulling tension is applied by the operator to the suture material 78a and 78b. The device 10 is then advanced down the taunt suture material 78a and 78b to a position proximal the tissue 80 being approximated, thereby "throwing" the knot 82.

Figure 11C:
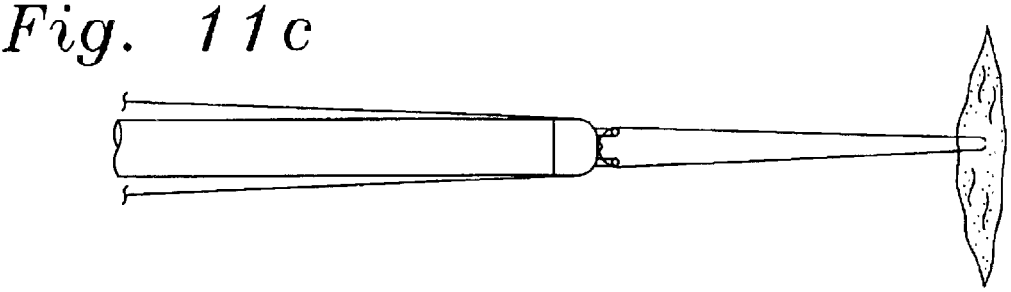
FIG. 11c is a side view of the knot pushing device of the present invention preparing to retain a knot formed in suture material.
Figure 11D:
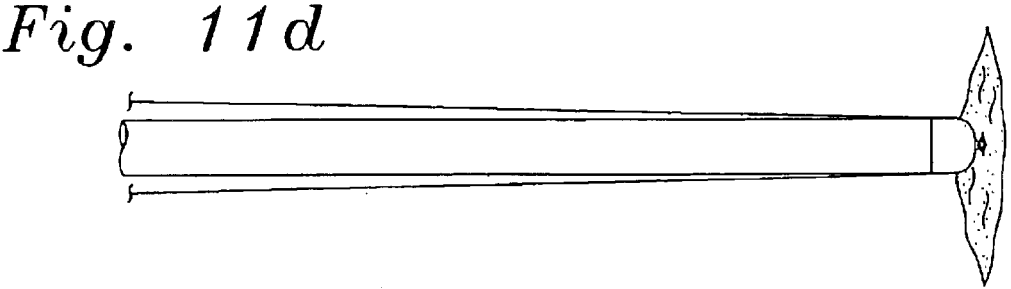
FIG. 11d is a side view of the knot pushing device of the present invention preparing to cut a knot formed in suture material.

The device can also be used to first retain the suture material prior to advancing the knot to the approximated tissue. Referring to FIGS. 3, 7, and 11c, the knot 82 may be retained in position by engaging the suture material 78a and 78b with the extendable retaining members 30a and 30b. To actuate the extendable retaining members 30a and 30b, the operator advances the pusher 52 towards the integral stop 48 thereby resulting in the slidable actuation piston 50 advancing into the handle body 42. The extendable retaining members 30a and 30b, which are in communication with the slidable actuation piston 50, are extended beyond the distal face 22 of the pushing interface 16. As the pusher 52 is advanced the cutting actuator 44 moves from the first position 46a within the cutting actuator receiver 46 to the second position 46b. As shown in FIG. 11c, the operator may then engage the suture material 78a and 78b with the retaining member 30a and 30b by positioning the excess suture material 78a and 78b within the suture receiving recess 26 along the pushing interface sidewalls 24a and 24b. Again the knot 82 is positioned proximate the knot positioning member 28, and a pulling tension is applied by the operator to the suture material 78a and 78b. In this embodiment, however, suture material 78a and 78b are placed between retaining members 30a and 30b and knot positioning member 28 as shown in FIG. 3. Once the retaining members 30a and 30b have engaged the suture material 78a and 78b, the operator releases the pressure applied to the pusher 52, thereby permitting the biasing member 76 to retract the retaining members 30a and 30b into the retaining member receivers 32a and 32b with the knot 82 and suture material 78a and 78b. Retraction of the retaining members 30a and 30b results in the cutting actuator 44, positioned within the cutting actuator receiver 46, retracting from the second position 46b to the first position 46a. Thereafter, the knot 82 is advanced or "thrown" proximal" the tissue 80 to be approximated. To release the device 10 from the attached suture the operator extends the retaining members 30a and 30b and disengages the suture material 78a and 78b. The device 10 may then be removed.

Figure 11E:
FIG. 11e is a side view of the approximated tissue.

Referring to FIGS. 4, 7, and 11d–11e, the present invention discloses a method of using the same device to extracorporeally form a knot, advance and attach the knot to an area of interest in vivo, and thereafter cut superfluous suture material. A portion of suture material 78a and 78b is secured to various tissue pieces 80 to be approximated. As shown in FIG. 11a, a knot 82 is extracoporeally formed in the suture material 78 using a standard bimanual technique. As detailed above, the knot 82 is retained by the retaining members 30a and 30b and advanced to a positioned proximal the tissue 80 to be repaired. To cut the surplus suture material 78a and 78b, the operator depresses the cutting actuator 44, thereby compressing the cuffing actuator biasing member 60 within the cutting actuator channel 58. The cutting actuator 44 is permitted to retract from a first position within the cutting actuator receiver 46a to a third position 46c. The biasing member 76 forces the slidable actuation piston 50 away from the handle body 42. The extendable retaining members further retract from into the retaining member receivers 32a and 32b and engage the cutting members 36a and 36b, resulting in the suture material 78a and 78b being cut. The device 10 and terminated suture material may then be removed from the body. FIG. 11e shows the approximated tissue.

In closing it is understood that the embodiments of the invention disclosed herein are illustrative of the principles of the invention. Accordingly, the present invention is not limited to that precisely as shown and described in the present invention.

What is claimed is:

1. A knot pushing device, comprising:
   an elongated body having a distal portion and a proximal portion, said distal portion comprising a pushing interface, said proximal portion attached to an actuation handle;
   the distal portion further comprising at least one generally L-shaped extendable retaining member located proximate to said pushing interface and configured to be positionable between an extended position extending distally from said distal portion of said elongated body, a retracted position, and a cutting position retracted proximately towards said elongated body, wherein the extendable retaining member comprises a first portion and a second portion, with the second portion being distal of and generally perpendicular to the first portion; and
   at least one cutting member configured to engage and cut suture material positioned adjacent the pushing interface when the extendable retaining member is in the cutting position.

2. The device of claim 1 wherein said elongated body is rigid.

3. The device of claim 1 wherein said elongated body is flexible.

4. The device of claim 1 wherein said elongated body is a catheter.

5. The device of claim 1 wherein said elongated body contains at least one lumen therein.

6. The device of claim 1 wherein said pushing interface further comprises a suture receiving recess.

7. The device of claim 1 wherein said pushing interface further comprises a knot positioning member.

8. The device of claim 1 wherein said at least one extendable retaining member is capable of engaging said at least one cutting member when positioned in said cutting position.

9. The device of claim 1 wherein said pushing interface further comprises at least one retainer member receiver.

10. The device of claim 9 wherein said at least one cutting member is positioned within said at least one retaining member receiver.

11. The device of claim 1 wherein said at least one cutting member comprises a blade.

12. A knot pushing device, comprising:
    an elongated body having a distal portion and a proximal portion, said distal portion comprising a pushing interface, said proximal portion attached to an actuation handle;
    a visualization device positioned on said pushing interface, the visualization device comprising radio-opaque or echo-genic material; and
    at least one cutting member capable of cutting suture material position on said pushing interface.

13. The device of claim 12 wherein said visualization device comprises echo-genic material.

14. The device of claim 12 wherein said visualization device comprises radio-opaque material.

15. A knot pushing device, comprising:
    an elongated body having distal portion and a proximal portion, said distal portion comprising a pushing interface, said proximal portion attached to an actuation handle;
    a visualization device positioned on said pushing interface, said visualization device comprising an ultrasonic probe; and
    at least one cutting member capable of cutting suture material positioned on said pushing interface.

16. A knot pushing device, comprising:
    an elongated body having a distal portion and a proximal portion, said distal portion comprising a pushing interface, said proximal portion attached to an actuation handle;
    a medicament applicator positioned on said pushing interface; and
    at least one cutting member capable of cutting suture material positioned on said pushing interface.

17. A knot pusher, comprising:
    an elongated body having a distal portion and a proximal portion, said distal portion comprising a pushing interface, said proximal portion attached to an actuation handle;
    the distal portion further comprising at least one extendable retaining member positioned proximate to said pushing interface and in communication with said actuation handle, said at least one extendable retaining member configured to controllably extend away from and retract towards said pushing interface; and
    at least one cutting member capable of cutting suture material positioned within said elongated body, wherein said at least one extendable retaining member is engageable with said at least one cutting member.

18. A method of applying a knot to a surgical site in vivo, comprising:
    placing suture material through tissue to be approximated;
    forming a knot extracorporeally in suture material;
    extending one or more generally L-shaped retaining members positioned on a knot pushing device distally from the knot pushing device to retain said suture material within a pushing interface;
    advancing said knot along said suture material with a knot pushing device;
    positioning said knot proximate tissue to be approximated with said knot pushing device; and
    retracting said retaining members toward at least one cutting member positioned within said knot pushing device to cut surplus suture material from said knot.

* * * * *